(12) United States Patent
Plank et al.

(10) Patent No.: US 12,256,728 B2
(45) Date of Patent: *Mar. 25, 2025

(54) SYSTEMS AND METHODS FOR VITAL ASSET TRANSPORT

(71) Applicant: CareDx Transplant Management, Inc., Brisbane, CA (US)

(72) Inventors: J. Scott Plank, Baltimore, MD (US); Paul F. Summers, Davidsonville, MD (US); Ryan Lupi, Charlottesville, VA (US)

(73) Assignee: CAREDX TRANSPLANT MANAGEMENT, INC., Brisbane, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/222,940

(22) Filed: Jul. 17, 2023

(65) Prior Publication Data
US 2023/0413804 A1 Dec. 28, 2023

Related U.S. Application Data

(63) Continuation of application No. 17/341,101, filed on Jun. 7, 2021, now Pat. No. 11,700,847.
(Continued)

(51) Int. Cl.
*G06Q 10/0832* (2023.01)
*A01N 1/00* (2006.01)
(Continued)

(52) U.S. Cl.
CPC ............. *A01N 1/00* (2013.01); *A01N 1/0263* (2013.01); *G06Q 10/0832* (2013.01); *G06Q 10/0833* (2013.01); *H04L 67/141* (2013.01)

(58) Field of Classification Search
CPC ........... G06Q 10/0832; G06Q 10/0833; G06Q 10/083
See application file for complete search history.

(56) References Cited

U.S. PATENT DOCUMENTS 5,586,438 A 12/1996 Fahy
6,736,836 B2 5/2004 Montgomery
(Continued)

FOREIGN PATENT DOCUMENTS

CA 3088986 A1 7/2019
CN 111867528 A 10/2020
(Continued)

OTHER PUBLICATIONS

Samper et al., "Portable Microfluidic Biosensing System for Real-Time Analysis of Microdialysate in Transplant Kidneys," Oct. 24, 2019, Analytical Chemistry, retrieved from https://pubs.acs.org/doi/10.1021/acs.analchem.9b03774 (Year: 2019).*
(Continued)

*Primary Examiner* — Rupangini Singh
*Assistant Examiner* — Bryan J Kirk
(74) *Attorney, Agent, or Firm* — Alston & Bird LLP (57) ABSTRACT

The invention is that of systems of methods for preserving vital assets such as human organs in transit. An exemplary system may include a central software application and processor for storing vital asset identifying information in a database and displaying real-time transit information in relation to the asset to authenticated users. Application programming interfaces are provided to allow authenticated users to monitor location and environmental data transmitted from the proximity of the asset to the central software application for processing and display on graphical user interfaces. An exemplary system enables methods of real-locating freight from a first to a second transportation asset
(Continued)

to avoid delays and prolonged exposures to adverse environmental conditions. In certain embodiments, unmanned aerial systems may be deployed to intervene in the transit channel and overcome such delays or exposures. In preferred embodiments, historical data is collected and analyzed to help predict human organ transplant outcomes.

20 Claims, 9 Drawing Sheets

Related U.S. Application Data (60) Provisional application No. 63/174,166, filed on Apr. 13, 2021, provisional application No. 63/035,704, filed on Jun. 6, 2020.

(51) Int. Cl.
*A01N 1/02* (2006.01)
*G06Q 10/0833* (2023.01)
*H04L 67/141* (2022.01)

(56) References Cited

U.S. PATENT DOCUMENTS

| | | |
|---|---|---|
| 8,323,954 B2 | 12/2012 | Kravitz et al. |
| 10,402,774 B1 * | 9/2019 | Phillips ............... G06N 20/00 |
| 2007/0095905 A1 * | 5/2007 | Kadaba ............... G07C 5/08 |
| | | 235/375 |
| 2011/0173023 A1 | 7/2011 | LeClair et al. |
| 2013/0173028 A1 | 7/2013 | Felty et al. |
| 2015/0264918 A1 | 9/2015 | Hassanein et al. |
| 2017/0086011 A1 * | 3/2017 | Neves ............... H04L 67/12 |
| 2019/0213538 A1 | 7/2019 | Bedout et al. |
| 2020/0226542 A1 * | 7/2020 | Lau ............... A61B 5/0022 |
| 2021/0037813 A1 * | 2/2021 | Scalea ............... G06Q 10/0832 |

FOREIGN PATENT DOCUMENTS

| | | |
|---|---|---|
| EP | 2599461 A1 | 5/2013 |
| JP | 2021511339 A | 5/2021 |
| WO | 2019143887 A1 | 7/2019 |

OTHER PUBLICATIONS

U.S. Appl. No. 17/341,101, Non-Final Office Action mailed Nov. 2, 2021.
U.S. Appl. No. 17/341,101, Notice of Allowance mailed Mar. 13, 2023.
U.S. Appl. No. 17/341,101, Non-Final Office Action mailed Jan. 26, 2023.

* cited by examiner

SYSTEMS AND METHODS FOR VITAL ASSET TRANSPORT

CROSS-REFERENCE TO RELATED APPLICATIONS

This application is a continuation of U.S. patent application Ser. No. 17/341,101, which claims the benefit of priority of U.S. Provisional Patent App. Ser. No. 63/035,704, filed on Jun. 6, 2020 and U.S. Provisional Patent App. Ser. No. 63/174,166, filed on Apr. 13, 2021. The contents of each of these related patent applications are hereby incorporated herein by reference in their entireties.

STATEMENT REGARDING FEDERALLY SPONSORED RESEARCH OR DEVELOPMENT

The invention described herein was developed without the benefit of federal funding.

BACKGROUND OF THE INVENTION

Human organs for transplantation are considered national assets by the federal government and as such there is a desire that they be donated fairly to recipients in need. This has led to the emergence of an increasingly complex distribution network for human organs, involving diverse transportation modalities, each introducing various logistic challenges that can cause an overall reduction of the quality of organs received by transplant surgeons within the network and even disqualification of organs destined for transplant due to delays and other problems associated with the various modes of transportation. Therefore, a growing need has arisen in the art for logistics solutions that reduce waste, save lives and help improve patient outcomes for transplant recipients.

Once a human organ has been removed from the body of a donor and is destined for transplantation in the body of a recipient, it may need to be transported over long distances and be subjected to a variety of different environmental conditions during transit. For example, changes in air pressure may be exerted upon an organ destined for transplant. The position of the organ within its packaging may change during transport. Air and land conditions may cause a vehicle transporting the organ to vibrate at various intensities. Particularly in the case of air travel, significant temperature fluctuations may occur in the organ's environment due to altitude changes, depending on the location of the organ on an aircraft. Furthermore, the organ may be subjected to impacts against its packaging as a result of, for example, a vehicle carrying it being driven over rough terrain. Additionally, varying levels of exposure to light may be applied to the organ during transport.

While it will be evident to one of ordinary skill in the art that these and other forces and changes therein may be applied against a human organ during transit, current means of monitoring these conditions to understand the exposure of an organ thereto fall short. Indeed, a transplant surgeon in receipt of a compatible organ for transplant in the body of a recipient may not be aware at all whether the organ has been subjected to potentially harmful environmental conditions that could affect the chances of a successful procedure. Therefore, there is a long felt need in the art for a means of ascertaining whether any adverse environmental conditions may have affected a human organ while in transit by monitoring and recording such conditions, thereby enabling transplant surgeons to better understand whether forces have been exerted upon an organ for transplant that may influence the outcome of transplants for recipients. It is one object of the invention of the present disclosure to provide such a means.

Systems and methods that leverage modern system architecture, software application development and communications protocols may be deployed to improve the overall success of any distribution network and thus may be leveraged to address the types of challenges that are unique to the organ transplant supply chain. Technology of this nature may indeed be practically integrated into physical and logical network infrastructures in order to enable a multi-partite human organ transplant network that allows for continuous visibility of individual human organ movements from donor to transplant recipient as well as intervention of physical assets useful in reducing transit times and the impact of environmental factors local to each organ as it moves from donor to recipient.

A central deficiency of the current systems and methods for distributing organs and other vital assets that are sensitive to transport times and temperatures (e.g., blood, tissue, bone and other biological materials) for transplant is the lack of an established communications and monitoring network that includes a comprehensive platform that allows for monitoring and communication of the status of all critical parameters of organ transport among all parties and physical assets involved, including but not limited to: systems maintained by organ sharing networks ("OSNs") and users thereof; systems maintained by organ procurement organizations ("OPOs") and donor hospitals, including live donor organizations, and users thereof; hospital systems and medical networks, including perfusion centers; environmental monitoring systems local to the freight and users thereof; physical transportation assets and their drivers, conductors or pilots; tracking systems used to direct and monitor traffic, such as air and ground traffic; and systems maintained by recipient facilities and personnel involved in the coordination and conduct of organ transplants, including those of regulatory agencies and testing laboratories. One of ordinary skill in the art will appreciate how the systems and methods described herein may also be leveraged as enterprise solutions within hospital networks and other medical networks, particularly the aspect of utilizing unmanned vehicles (e.g., drones, self-driving carrier carts) to move freight securely between locations in the network.

Another deficiency of the current systems and methods for distributing organs for transplant is the lack of a validated physical data repository where information on organ quality may be correlated with information generated from within the transplant distribution network and from patient outcomes. In addition to medical information collected in the past, such as donor and recipient patient histories, immunological information and time between the chilling of the organ after its blood supply has been cut off ("clamp time") and the warming of the organ when its blood supply is restored (known as cold ischemic time, or "CIT"), research has demonstrated that factors at play in the distribution network may play a part in transplant recipient success rates or outcomes. Such factors may include but are not limited to the temperature, barometric pressure, vibration, acceleration, impact force, container orientation and light exposure affecting a human organ in transit. It is an object of the invention to generate a better understanding of how all such factors individually and collectively impact organ quality and patient outcomes through machine learning and statistical validation by academic experts.

Another deficiency of current systems and methods for delivering organs for transplant is a lack of any method of intelligent transportation asset allocation within the transplant distribution network. This is an important challenge, as sometimes the objective of fairly matching organs between donors and recipients results in long travel times and distances depending where each are located. This objective, while noble, can lead to waste when a selected recipient is a long distance from the donor site. When a matching organ must travel long distances CIT is obviously increased, and in some cases this problem may be exacerbated by unforeseen delays that go unmonitored within the network and lead to waste as well as patient mortality. With the emergence of machine learning, there is an opportunity to meet a need in the art for better methods of organ transportation asset allocation that aim to reduce organ waste and patient mortality.

Another shortcoming of current systems and methods for delivering organs for transplant is the cost associated with increased transit times in terms of man hours, hospital hours, equipment depreciation and fuel. There is also an increased probability of malfunction and accidents where logistics are not optimal. Moreover, it is incredibly expensive to prepare and staff an operating room for an organ transplant only to have the operation delayed without communication to hospital staff. As such, it would be useful for the clinical staff to be aware of transit delays because it may enable them to utilize the clinical space to conduct other procedures during the delay period, for example, thereby improving hospital efficiency.

Another shortcoming of current systems and methods of human organ transportation is the use of commercial land and air transportation means that are not able to prioritize organ shipments in a way that optimizes the likelihood of successful deliveries. An organ may be placed in a cargo hold that is subjected to temperatures well below freezing in the case of air and ground transportation alike without any means of assuring more moderate temperature exposures or rerouting the packages to a more suitable route, or simply to a more suitable location within a transit craft or to a more suitable craft destined for the same location. It is one object of the invention described herein to overcome these problems. Air traffic and automobile traffic is often subject to delays due to weather, accidents and other unexpected contingencies that arise routinely. Thus, there is a need in the art for intervention in the various transit channels and reallocation of human organs to more suitable means of transportation.

These and other costly shortcomings of current systems and methods for managing the supply chain of human organs for transplantation will be readily apparent to one of ordinary skill in the art, as well as the resulting need for the innovations described herein.

BRIEF SUMMARY OF THE INVENTION

The systems and methods according to the present disclosure represent innovations that offer significant benefits over existing transplantation network infrastructures. The present disclosure describes systems comprising physical components and architectures that allow for the practical integration of software programs into a network that implements machine learning to optimize logistics and allocate the assets responsible for organ transportation according to methods designed to improve outcomes and save lives. In certain embodiments, a system architecture is utilized to establish and centralize communications within an organ transplantation and distribution network in order to provide visibility to the movement of assets through the supply chain and enable rerouting and the deployment of assets for reallocation when necessary to improve the likelihood of successful transplantations.

In certain embodiments, the systems and methods described herein comprise at least one software application tangibly stored on a non-transitory computer readable medium in network communication with at least one application database and at least one computer processor. Network communications are established with other systems through at least one corresponding application program interface ("API") in order to leverage information from sources external to a system as described herein for optimal functionality. A software application as described herein comprises instructions which when carried out by a processor cause the processor to synthesize outputs from multiple system inputs and generate real-time displays that provide continuous visibility of individual human organ movements from donor to transplant recipient, in addition to other functionalities described throughout this disclosure. In certain embodiments, a real-time display is visible on a user interface, preferably a graphical user interface ("GUI"). In certain embodiments, the methods described herein comprise the reallocation of human organs to alternative transportation assets or rerouting based on user observations of system outputs.

The systems and methods of the present disclosure enable a centralized platform for distributing organs for transplant that allows for monitoring and communication of the status of all critical parameters among all authorized, responsible parties and physical assets involved, including but not limited to: systems maintained by OSNs and users thereof; systems maintained by OPOs and donor hospitals and users thereof; environmental monitoring systems local to the freight and users thereof; physical transportation assets and their drivers, conductors or pilots; tracking systems used to direct and monitor traffic; and systems maintained by recipient facilities and personnel involved in the coordination and conduct of organ transplant procedures, including those of regulatory agencies and testing laboratories. The invention of the present disclosure may utilize proprietary tracking technologies or commercial off-the-shelf tracking solutions to monitor the location and condition of packages, or use a mobile phone of courier personnel, for example, to track the freight when a proprietary system goes offline. In certain embodiments, the time for a courier to arrive at an origin and pick up a package may be calculated in advance of an associated shipment plan.

In certain embodiments, the systems and methods of the present disclosure comprise at least one database comprising information input manually or extracted from at least one peripheral information source, wherein the at least one database comprises information relevant to the suitability of human organs for transplantation and the origins of said human organs. In certain embodiments, the at least one database may comprise a relational database. In certain embodiments, the at least one database further comprises information generated from within the transplant distribution network and from patient outcomes for transplant recipients receiving organs represented within the at least one database. In certain embodiments, such information comprises information on temperatures, barometric pressures, vibrations, acceleration, impact forces, container orientations and light exposures to which human organs have been subjected during transit.

In certain embodiments, the methods of the present disclosure enable optimized asset allocation within a transplant distribution network. In certain embodiments, the asset allocation may be optimized by reducing travel distances. In certain embodiments, the asset allocation may be optimized by reducing CIT for a transplantable human organ during transit. In certain embodiments, asset allocation methods may be optimized through machine learning. In certain embodiments, the asset allocation comprises organ allocation that reduces organ waste, transplant patient mortality or costs associated with the transportation or transplantation of human organs for transplant. In certain embodiments, the asset allocation is a reallocation of an asset in transit from an automobile, train or manned aircraft to an unmanned aerial system ("UAS").

An exemplary embodiment of the present invention may comprise a specialized container for the transportation of organs with a system for monitoring the environmental conditions of a human organ destined for transplantation in the body of a recipient while in transit from donor to recipient. In preferred embodiments, the invention further comprises a means for reducing or minimizing the effects of certain environmental conditions on the contained organ. The invention of the present disclosure is not limited merely to determining the most appropriate mode of transport, but further enables carefully selecting a particular type of vehicle, e.g., a plane with a heated cargo hold versus unheated. In addition, e.g., when a flight is missed, the system may revert back to ground tracking until a new flight is scheduled. In certain embodiments, a human organ container may comprise a motherboard, as will be familiar to one of ordinary skill in the art, electrically connected to a power source (e.g., battery) and one or more sensors, all within a system compartment of a container as described herein. In preferred embodiments, the invention of the present disclosure is further equipped with a means for transmitting and receiving information, such as but not limited to a transceiver for sending and receiving data to and from an included tracker, wherein the tracker enables transportation teams to know the location of an organ being transported according to the present disclosure, and also the nature of the organ environment, via sensors in communication with the tracker via the transceiver.

In an exemplary embodiment, a container according to the present disclosure comprises an organ compartment for containing an organ within a transport medium, such as a liquid medium, suitable for immersion of a human organ contained therein. In preferred embodiments, a medium is utilized comprising properties that preserve the organ immersed. In preferred embodiments, an organ compartment and system compartment are combined to form an organ transport container, the organ compartment having a lid that fits the organ compartment opposite the system compartment to prevent leakage of transport medium from the organ compartment. The advantages of the invention described herein will become more apparent from the detailed description provided below.

DETAILED DESCRIPTION OF THE INVENTION

In certain embodiments, systems and methods are described herein for real-time logistics management, geospatial locating, transportation routing and rerouting, transportation asset allocation and reallocation and environmental monitoring of vital freight. In preferred embodiments, systems and methods of the present disclosure are optimized for use within distribution networks for human organs destined for transplantation. The systems described herein combine physical component architectures to provide network infrastructures well-suited for these purposes. The methods described herein take advantage of said systems in order to reduce the overall costs associated with the movement of vital freight such as human organs and the waste associated with losses thereof, thereby fulfilling a long felt need in the art to accomplish these goals in the public interest. In the following description, many specific details are explained for illustrative purposes. It will be readily apparent to one of ordinary skill in the art, however, that the present invention encompasses many embodiments that may share some common elements but not others. For example, certain assets such as semiconductor materials are incredibly sensitive to light and should be monitored for exposure, while biological materials may be more sensitive to temperature but not need to be monitored for light exposure. The drawings accompanying this description are provided for the purposes of illustration as well and should be considered exemplary but not comprehensive representations of the invention of the present disclosure.

For example, embodiments of the present invention are described in large part herein in the context of the allocation of human organs from donors to transplant recipients; the transportation and geospatial tracking of the same; the rerouting and reallocation of the freight, comprising in particular reallocation to UAS assets from other transport modes; the environmental monitoring of freight, and in particular vital freight such as human organs; and the development of a relational database that may be used to facilitate machine learning and inform the field on methods for improving the quality of human organs arriving at transplant sites and associated patient outcomes. The invention is not limited to this context, however. For example, other embodiments may fall within the context of transporting perishable goods, goods useful in the field of public safety, or other freight that is sensitive to environmental inputs and transit time, such as biomaterials or semiconductor materials. All of these examples serve to illustrate the broader utility of the present invention and none should be considered as limiting the practical integration of the systems and methods described herein into an appropriate solution. Reference is now made to the accompanying drawings.

Figure 1A:
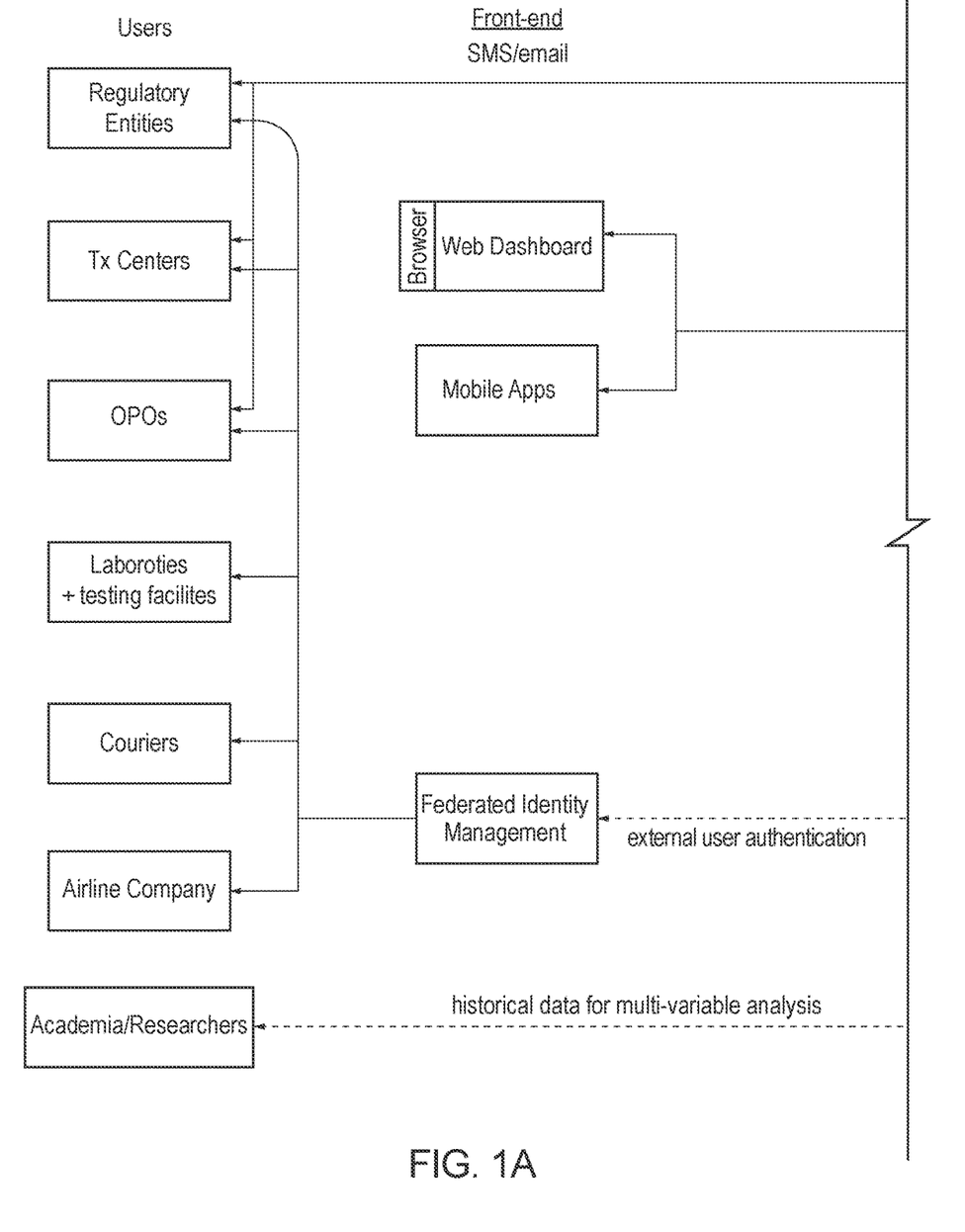
FIG. 1A illustrates authenticated users in network communication with a system according to an embodiment of the present invention, including via available web dashboard and mobile software application.
Figure 1B:
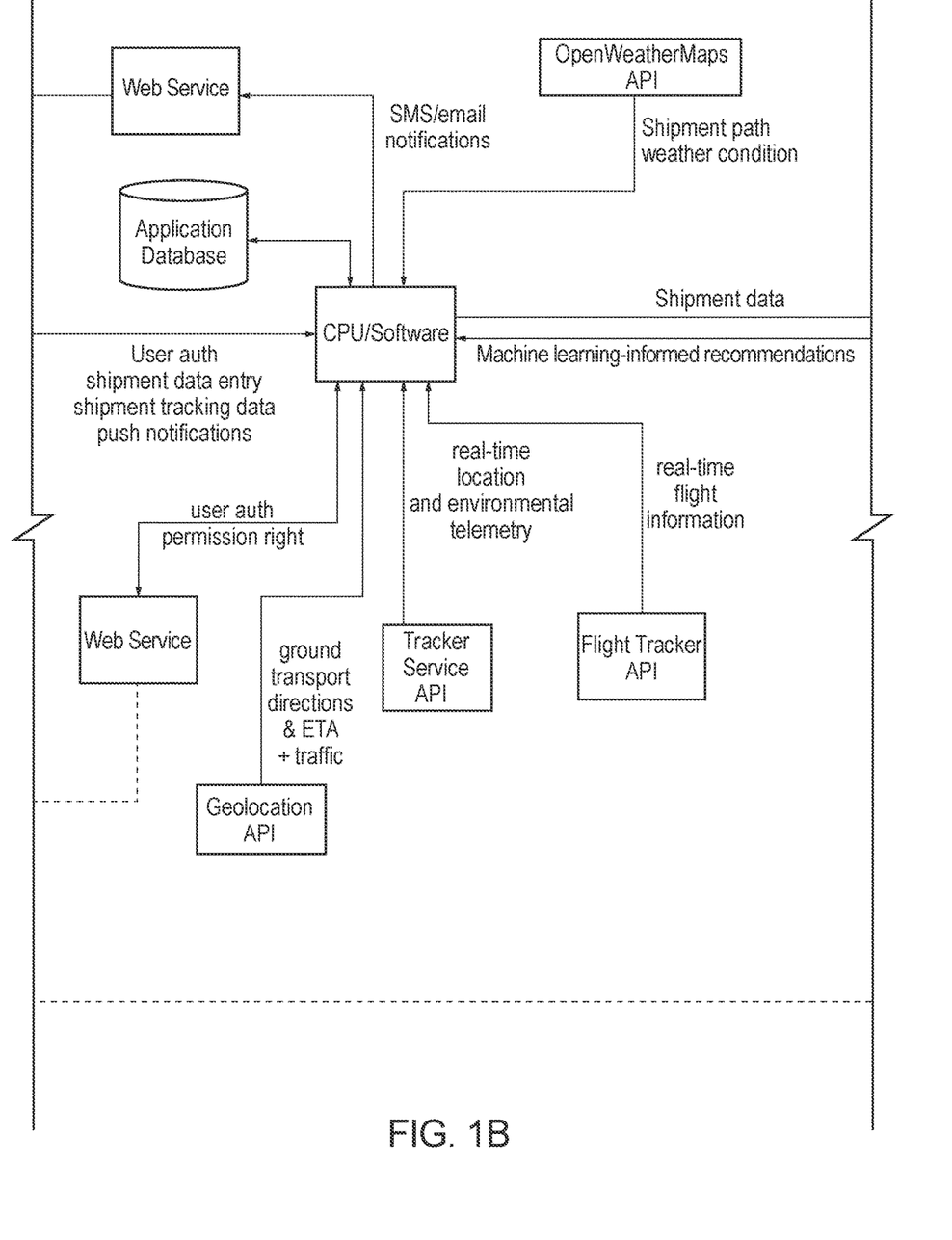
FIG. 1B illustrates major system components of an embodiment of the present invention, continuing from FIG. 1A.
Figure 1C:
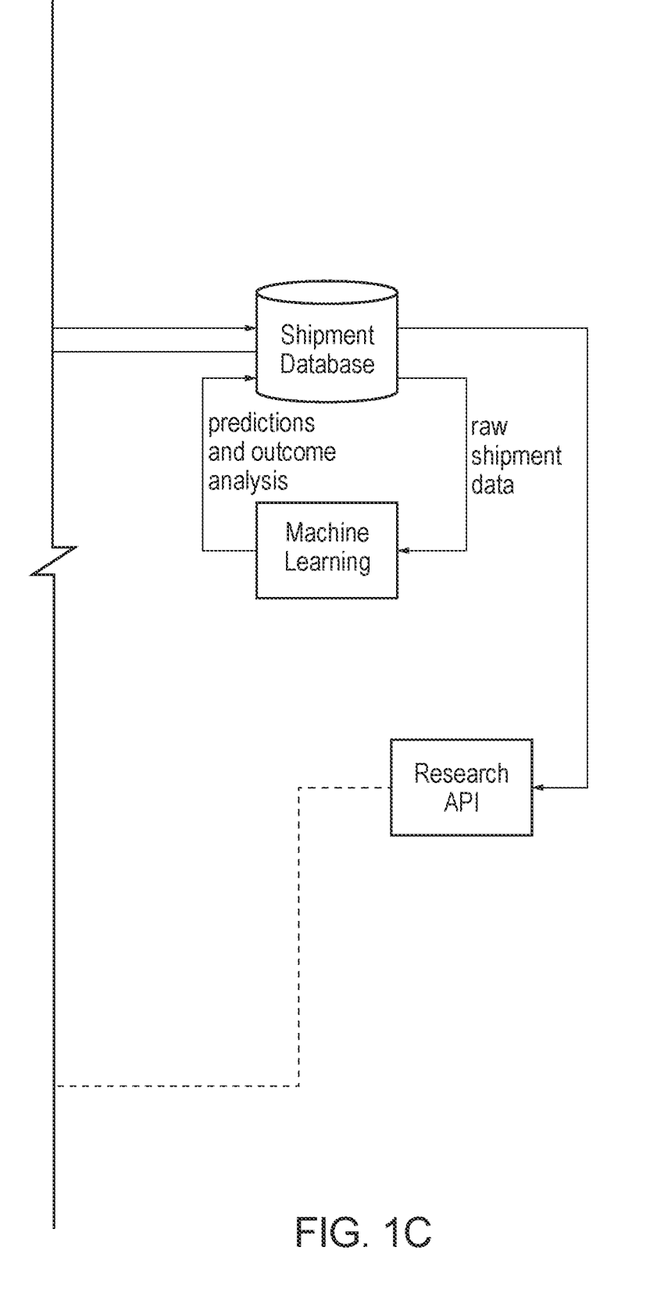
FIG. 1C illustrates a data collection and machine learning environment according to one aspect of the present invention, in network communication with major system components as well as other end points.

FIGS. 1A-1C represent various aspects of an exemplary system as described herein. Beginning with FIG. 1B, a processor such as a central processing unit ("CPU") capable of executing instructions contained in a software program in order to transform data contained in an application database are at the center of the system architecture. The software program may be installed on a computer for local processing, or may reside elsewhere, such as on a remote server in communication with the processor. These components may be in network communication with multiple other system inputs through various installed APIs. In certain exemplary embodiments of the present invention, users of a system as described herein include participants in the human organ transplant supply chain who may obtain access to the system via user authentication methodologies that will be familiar to one of ordinary skill in the art, such as authentication using a web service.

After gaining authenticated access to the system, a user as described above may enter pertinent shipment data, including but not limited to donor information, organ type, donor hospital, donor OPO, recipient information, recipient transplant center, ground transport information, flight information and laboratory and testing information. This may be done by accessing an Internet website and utilizing a web dashboard, or via downloadable mobile applications. This data is stored within an application database along with data collected from external data sources such as but not limited to weather maps, flight trackers, freight trackers, geolocation systems and user inputs. Each of these external data sources are in communication with the processor over an installed system API. These data, which are dynamic in nature, are also stored within the application database and updated as the shipments move.

As each shipment moves and the application database is updated, stakeholders may be alerted as to the status and location of each shipment via short message service (SMS) text notifications, or updates may be viewed via the website or mobile application. In this way all the relevant stakeholders in a shipment have real-time access to information about the shipment, including status, condition and location, and authorized stakeholders may reallocate the shipment to a different transportation asset, for example, if delays or unacceptable environmental conditions appear imminent.

Users of an exemplary system as shown in FIGS. 1A-1C may include, for example, regulatory entities, transplant centers (represented "Tx Centers"), OPOs, live donor centers, laboratories and testing facilities, couriers and airline companies or UAS fleet management companies. A system according to the present invention may also be employed for in-network logistics management of vital asset transport, allowing nodes within the network to order and track deliveries of vital freight via various manned or unmanned systems, such as UAS or unmanned highway vehicles.

Security is provided through federated authentication protocols as will be understood by one of ordinary skill in the art. Users may access a system as described herein through a web dashboard available on the Internet or an intranet, or via downloadable mobile application, as will be appreciated by one of ordinary skill in the art. A web service may be leveraged for outbound communications to users such as notifications regarding freight location information, weather information or transit delay notification. Meanwhile inbound communications may be enabled by web or mobile application interface including a user-friendly GUI, to allow for direct and group chat, SMS texts, emails, push notifications and video chat, which is particularly important in cases where doctor-to-doctor video interactions promote better methods of organ harvesting from donors. These communication paths may enable methods as described herein, for example, reallocation and rerouting methods that are not currently available within the human organ supply chain and certain other supply chains alike.

Turning now to FIG. 1C, a shipment database may be provided within a system of the present invention to allow for the collection of data related to the freight shipped, such as a human organ, its transit time, delays, rerouting, reallocation, comparison of scheduled versus actual delivery, and data related to clinical success of a transplant of an organ transported using methods described herein. The collected data may then be processed according to instructions provided by a machine learning program to enable the development of predictive analytics, the information outputs of which may be validated by academic researchers as depicted in FIG. 1A. It is an object of the invention to help improve overall clinical outcomes based on such machine learning techniques. This information can then be accessed by the central software program, processed and stored within the application database in order to better inform stakeholders on courier selection, transit routes and the like.

Present within the broader network is an OSN, which comprises a database containing identifying information for each asset (i.e., transplantable organ) having corresponding data within the database. The data maintained by an OSN is obtained from hospitals and other external data sources that identify the assets for the OSN. Also present within the broader network are OPOs (or living donor organizations), which maintain systems that communicate directly with donor hospitals in order to engage in the procurement process when donor organs become available for transplantation. Also present within the broader network are systems maintained by third parties for the tracking of organs as they move throughout the transit channels from donor to recipient. Such systems may utilize satellite-based technologies such as global positioning systems ("GPS") for the geospatial tracking of freight by providing tracker hardware that follows the freight through the transit channels, allowing the freight to be located throughout the process as needed. Such third-party systems in the current state of the art are not in communication with systems of the OSNs or OPOs. It is one object of the present invention to make these network connections.

Various modes of transportation are employed throughout a transplant distribution network depending on the required movement of freight. Ground transportation is typically the first mode of transportation employed, i.e., a courier or shipping company will receive a transplantable organ in a package comprising a tracker or may install the tracker with the freight. The next step is typically to either deliver the package to its destination, i.e., a hospital housing the recipient, or more often, to an airport, where the package is handed off to airline personnel for loading onto a primary flight. The destination of the primary flight is typically an airport, where the package may be passed to other airline personnel for a connecting flight to its land destination, or another ground transportation provider. Ground transportation is typically the final mode of transportation employed to get the asset from its final airport destination to its ultimate destination where its transplantation into the recipient will take place. It will be apparent to one of ordinary skill in the art that this current state of transplant distribution network management may be rife with all manner of costly delays and mistakes.

In one aspect of the invention, the deployment of UAS within the transportation channels as alternative modalities to ground and air transport means deployed within current transplant distribution networks may be leveraged to eliminate delays. UAS are key elements of certain exemplary systems and methods of the present invention. The deployment of UAS for this purpose may be a cost-saving and indeed life-saving step of a method as described herein for increasing transplant success rates. For example, UAS may be deployed to an inner-city donor hospital for seamless delivery across town to a recipient hospital, or delivery to a shipping line or airport for handoff to long distance carriers. The advantages of UAS deployment will be obvious to one of ordinary skill in the art, yet it is another object of the present invention to increase the use of UAS for organ transport due to the many problems that arise within the transit channels that could be eliminated by well managed UAS deployment within a system as described herein. In one aspect of the invention, UAS deployed for this purpose are type-certified by the Federal Aviation Administration (FAA) in order to gain better operational flexibility and rapidly cover longer distances.

It is an object of the present invention to provide systems and methods for the establishment and centralization of communications between and among all systems active in the broader transplantation network and enable the reallocation of assets in transit, e.g., to UAS, when problems arise that have the potential to cause asset loss, patient mortality or both. It is the absence of such systems and methods in the current state in the art that is largely responsible for the inefficiency and waste occurring within the supply chain that results in organ recipient mortality and poor transplant outcomes, the latter of which are not predictable according to the current state of the art. It is another object of the present invention to leverage the establishment and centralization of communications between and among all systems within the broader network to generate a database to which machine learning techniques can be applied, thereby creating a network that provides feedback into the system to avoid undesirable outcomes such as these.

The selected physical components and subsystems and communication channels and interfaces comprise APIs that may be installed on the various devices used to connect to the network, such as computers, smartphones and tablets. In an exemplary system, APIs capable of communicating with the central processor and software program are stored on a non-transitory computer readable medium in communication and in network communication therewith. These interfaces enable the network to remain secure, and allows all authenticated stakeholders in a given shipment to track the shipment, receive updates and communicate with one another. Standard communications protocols such as Internet protocol ("IP") and the like serve as underlying infrastructures that enable buildout and operation of a system of the present invention.

Turning back to FIG. 1C, the subsystem comprising machine learning algorithms tangibly stored on a non-transitory computer readable medium, wherein the machine learning algorithms cause a processor to execute multiple value-add method steps according to the invention described herein. The subsystem may be in communication with the central processor and software program along with OPOs, donor hospitals, tracking companies and other organizations from which user inputs originate. A processor of the subsystem may then execute the instructions stored within the subsystem software application by, for example, by apply machine learning algorithms to generate information useful to those involved in the transplant distribution network.

In certain embodiments, a GUI installed on a computer familiar to one of ordinary skill in the art, such as a desktop, laptop, tablet or smartphone computer, following appropriate user authentication via secure login, presents the movement of assets about the transplant distribution network in a programmable manner, subject to preferences that may be selected by a user. In some embodiments, at least one software application of a system of the present invention may access and present geospatial data from a third-party provider and convert that data to a visual interactive map that may be viewed by a user. Authenticated users, depending on defined roles, may access one or more of data from an OSN database; data from an OPO database; data from a system or subsystem database of the present invention; or GPS data from a third-party tracking company. In preferred embodiments, users may display as much or as little of the accessible data as is needed to achieve an objective. For example, a transplant coordinator at a transplant hospital may be awaiting a specific organ in transit and filter a view of a map presented on an installed GUI to track the shipment in real-time and monitor its estimated time of arrival ("ETA"). One of ordinary skill in the art will appreciate that real-time tracking enables the transplant coordinator of this example to identify when delays occur that could compromise the objective of successful transplantation into the recipient at the transplant hospital. In certain embodiments, a system of the present invention may enable geofencing methods useful in identifying the location of an asset in transit and comparing that location to the location that would be expected based on the transit schedule of the asset to identify delays. Others within the transplant distribution network may also see these developments, and each may communicate with the other to order reallocation strategies where unacceptable delays are likely.

In certain embodiments, a UAS fleet operator within the network may order deployment of a UAS based on the geospatial coordinates of a tracked package that has been delayed in transit. For example, if an asset has arrived at an airport but cannot be timely transported by ground transportation to the transplant hospital due to traffic, weather, road closures or other emergencies, a fleet operator in network may deploy a UAS to the airport to receive the asset and transport it safely and timely to the transplant hospital, enabling a transplantation that may not have otherwise been possible due to extended CIT.

In some embodiments, a system of the present invention comprises one or more environmental sensors for monitoring the physical surroundings of a human organ during transport. Such a sensor may comprise a sensor selected from the group consisting of temperature sensors, pressure sensors, vibration sensors, acceleration sensors, impact force sensors, orientation sensors, light sensors, altitude sensors and combinations thereof. In certain embodiments, the one or more environmental sensors may be in communication, i.e., cellular or wireless communication, with a software application of a system of the present invention, which may in turn cause a processor to execute instructions stored therein to save data obtained by the one or more sensors into a database of a system of the present disclosure. In preferred embodiments, the data obtained by the one or more sensors represents multiple measurements of each monitored environmental parameter taken at different time points along the journey of the organ and may be stored in a relational database for analysis.

Two-way user authentication is provided by users of a system of the present invention as well as users of OSN systems to facilitate secure interaction and data sharing. OSN data is transmitted to a system of the present invention via an API, resulting in processing according to software program instructions according to the present invention and secure storage. Donor identification transplant surgical team data and other useful data may be stored for centralized access within a system of the present disclosure. OPOs may transmit shipping information corresponding to the various assets represented within the database via installed API for storage and access by other systems in the network. OPOs among others may track the assets they have procured using this system and network design.

Secure access may be provided to OSN and OPO data by other participants in the human organ supply chain utilizing the present invention. One object of a system of the present disclosure is to ensure accurate correspondence between the asset information received from the OSN and OPOs and tracker information, i.e., so each tracker being used to monitor progress of the asset from donor to recipient bears a unique "signature" that matches the asset with which it travels. In certain embodiments, a tracker may be a component of a system of the present disclosure, as represented by communication between the tracker service API and central processor and software program as depicted in FIG. 1B. The trackers may be third-party trackers, a feature enabled by the present invention that is not present in the current state of the art. In this way, a system of the present invention provides a means not available before that allows for synchronization of the activities of the OSN, OPOs, participating hospitals and participating transportation, logistics and tracking operations, wherein one such tracking operation may be practically integrated within the system itself.

A shipment database as illustrated in FIG. 1C comprises data on the environmental pressures exerted on organs in transit, the transportation data associated with the journeys and the outcomes for patients receiving each organ. The development of such a database enables a key objective of the present invention. The applicant has observed that environmental pressures exerted upon organs in transit—in addition to elevated CIT—may have adverse impacts on the suitability of the organs for transplantation once they reach their destinations. For example, despite the cold packaging of organs for transplant, extreme temperatures such as extreme heat as may be experienced, e.g., in the back of a box truck traveling in South Florida in the summer months, or extreme cold as may be experienced within a cargo hold of a commercial airliner traveling at 30,000 feet above sea level, may compromise the integrity of the packaged organ with respect to its suitability for transplant. Other physical pressures may also have effects.

Figure 2:
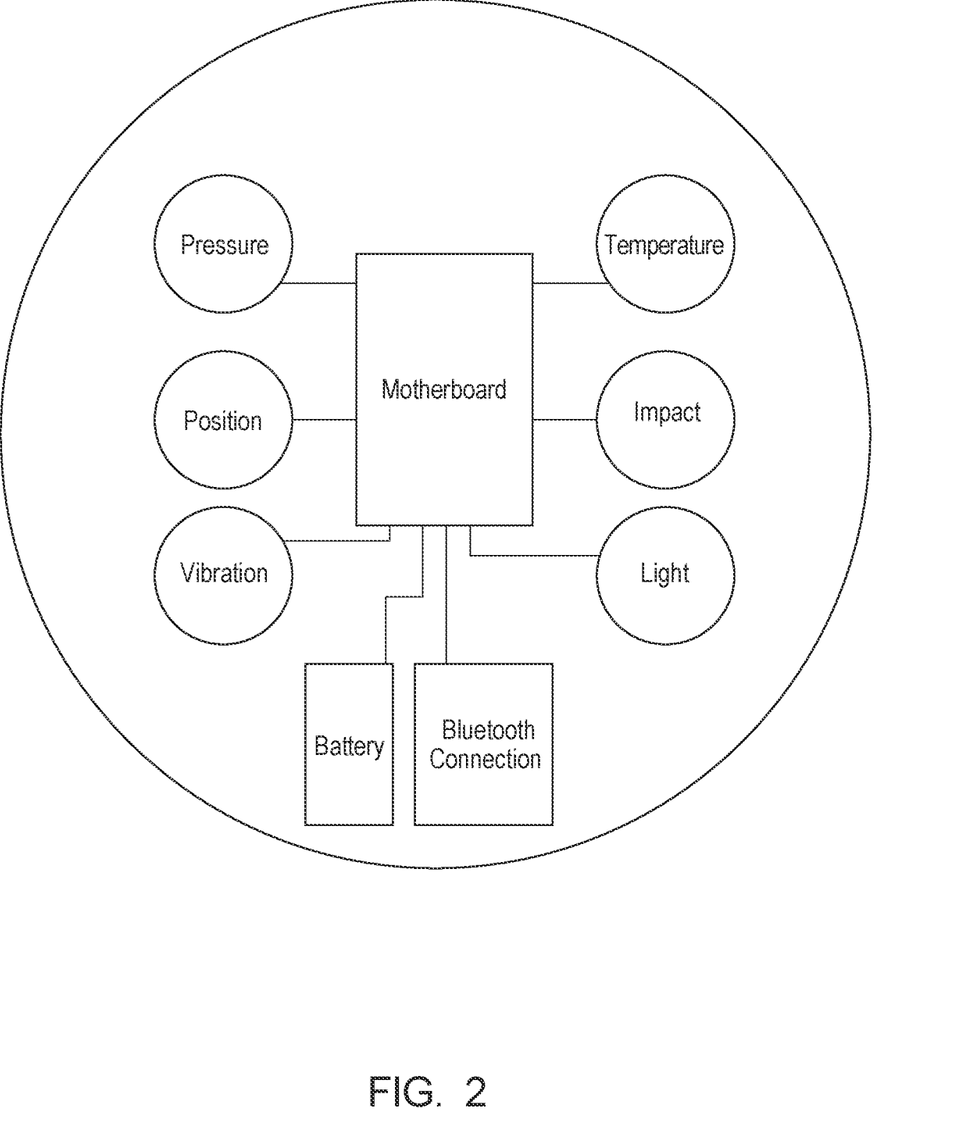
FIG. 2 illustrates a top-down schematic view of an environmental sensing system compartment according to an illustrative embodiment of the present invention.

FIG. 2 illustrates an embodiment of an environmental sensing system compartment according to the present invention, represented as having multiple sensors electrically connected to a motherboard, which is in turn connected to a battery for power. In this embodiment, sensors of pressure, position, vibration, temperature, light and impact are electrically connected to the motherboard to enable the collection and recordation of data. In the illustrative embodiment of FIG. 2, a battery is present within the system compartment as an external power source with respect to the motherboard, although one of ordinary skill in the art will appreciate that a battery or other suitable power source may be included as a motherboard component.

The embodiment of FIG. 2 includes a transceiver indicated as a Bluetooth connection, Bluetooth being but one of many possible communication standards that can be leveraged in order to establish a communication path between the motherboard and one or more external devices, enabling the exchange of data therebetween. In particular, any validated wireless networking technology may be employed. For example, Wi-Fi may be employed where it is possible to establish Wi-Fi networks within the transportation channel of interest. While wired networks may be used where a transceiver and external device are in close physical proximity to one another, the use of wireless communication technologies include advantages that will be evident to one of ordinary skill in the art.

Figure 3:
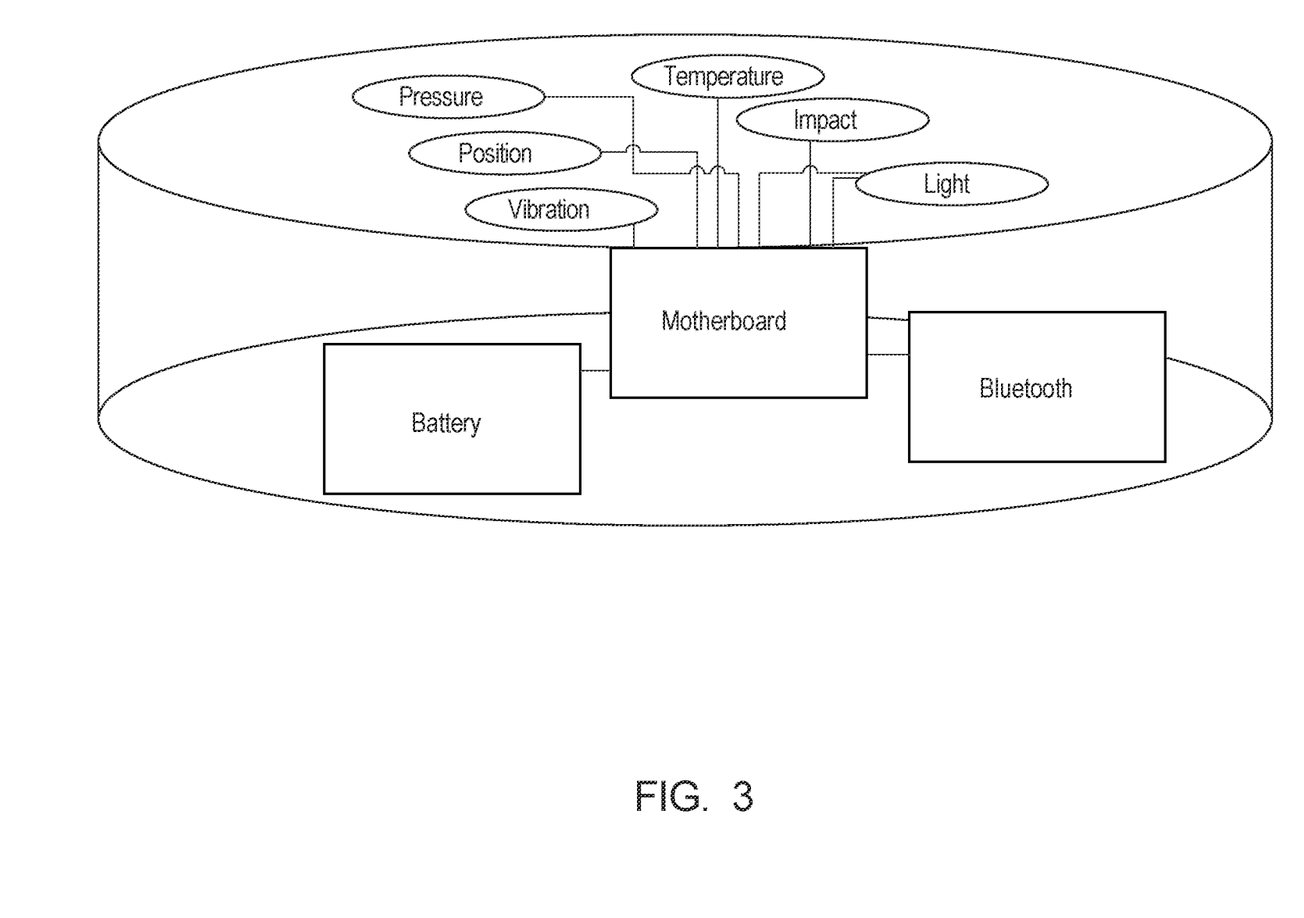
FIG. 3 illustrates a top perspective view of the environmental sensing system compartment shown in FIG. 2.
Figure 4:
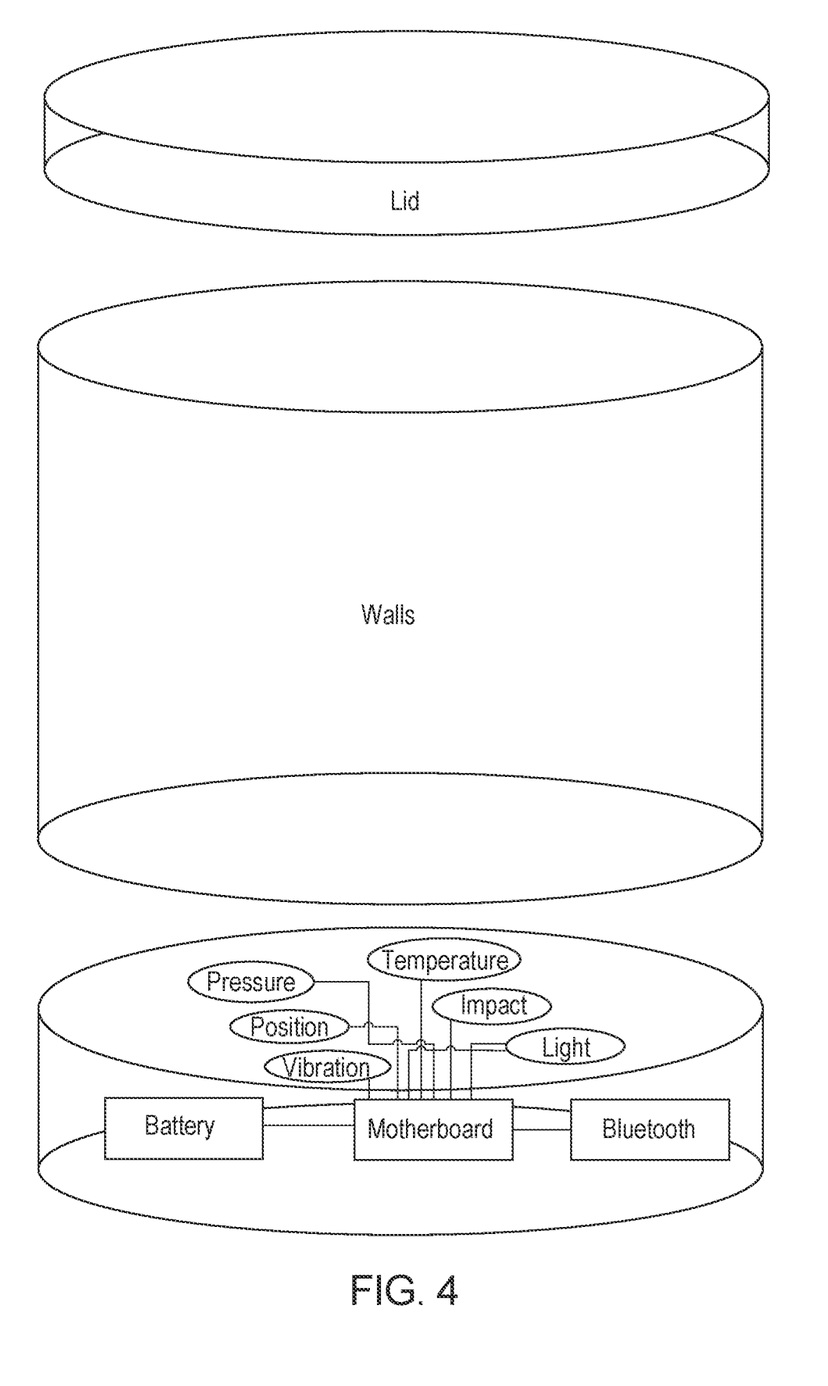
FIG. 4 illustrates a cylindrical walled organ compartment according to an embodiment of the present invention which operates to contain an organ between an environmental sensing system compartment and a lid as shown in expanded view.

Turning now to FIG. 3, a system compartment as depicted from top view in FIG. 3 is illustrated in perspective view, wherein the illustrative embodiment shown is configured as a cylinder, the upper diameter of which is preferably similar to that of an organ compartment as shown above a system compartment in FIG. 4, such that an organ compartment and system compartment, along with a lid, may unitized by suitable means as will be appreciated by one of ordinary skill in the art. Illustrated in FIG. 4 is an expanded view of a cylindrical embodiment of an organ transport container according to the present invention, wherein the organ compartment is walled for the containment of an organ in transport medium and is securable to a system compartment beneath and lid above. As will be evident to one of ordinary skill in the art, the interfaces between the organ compartment and lid, as well as organ compartment and system compartment, must comprise a seal to prevent leakage of transport medium and possible compromise of the organ contained as a result of such leakage. Also, the size, shape and configuration are not critical; rather, as long as the freight is appropriately packaged for travel and in proximity of location and environmental trackers, the system will enable the methods described herein.

Figure 5:
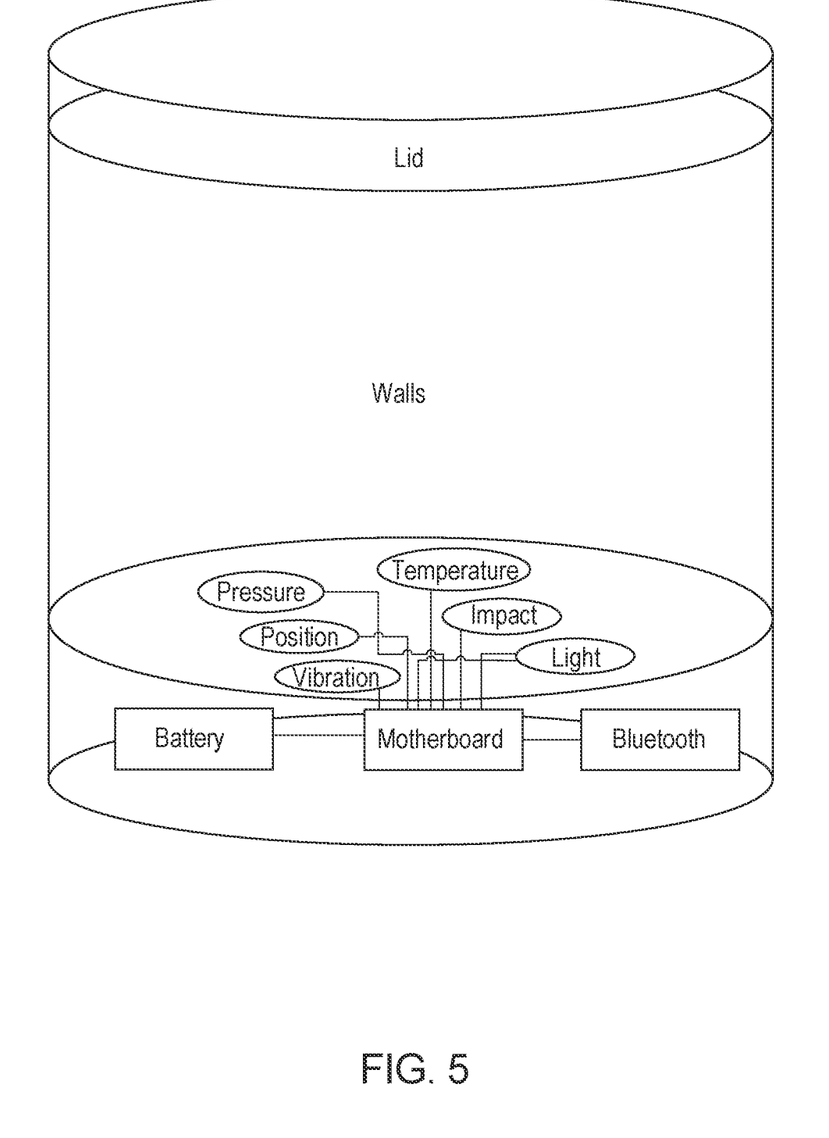
FIG. 5 illustrates the lid, organ compartment and environmental sensing system compartment according to FIG. 4, integrated together into an exemplary organ transport container as described herein.
Figure 6:
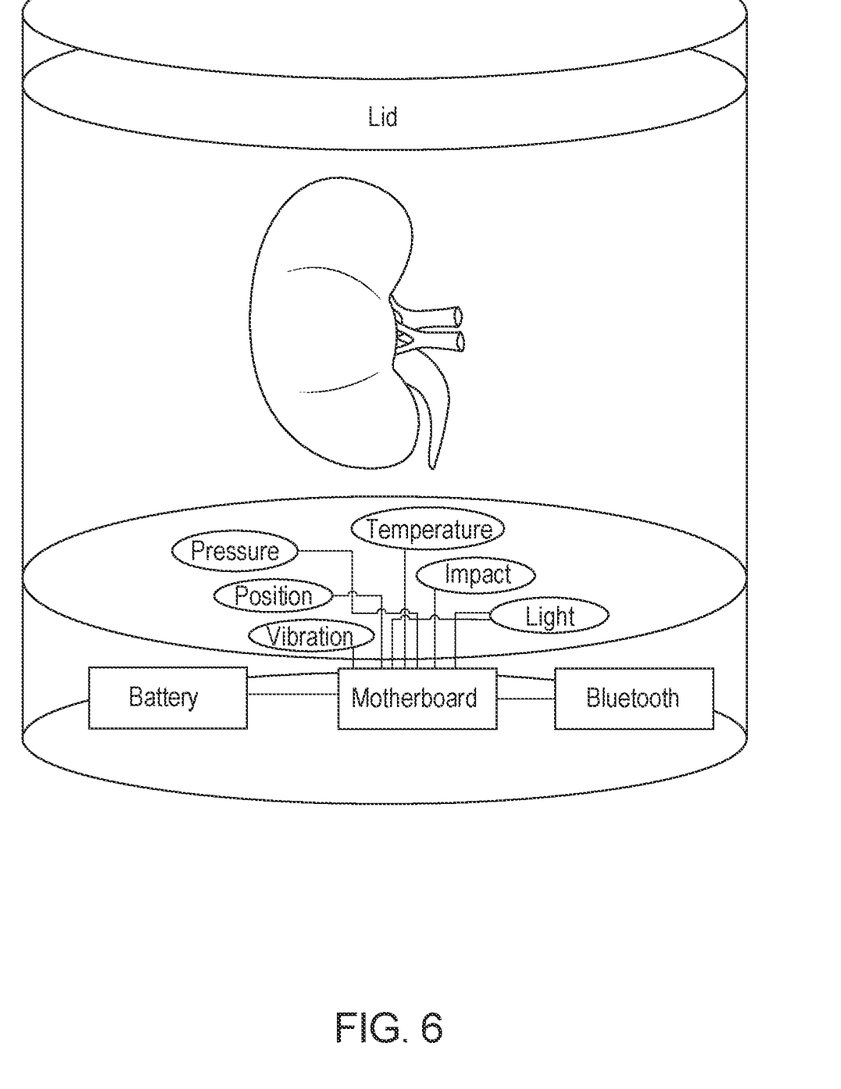
FIG. 6 is a reproduction of FIG. 5, with an organ, in this case a human kidney, shown suspended in transport medium within an organ compartment according to the present invention.

One of ordinary skill in the art will also appreciate that while seals are necessary to prevent leakage of transport medium, it is possible that each compartment and lid might be sterilized for reuse, so a temporary means of creating seals to guard against leakage during transport may be desirable. For example, each component of an organ transport container according to the present invention may be configured with threads, allowing the lid to be threaded over the organ compartment, and the organ compartment to be threaded over the system compartment. In certain embodiments, gaskets may be provided at each interface to create better seals than threads alone. Threaded components not only enable component separation for reuse, but also allow for ease of use in terms of packing an organ for shipment and removing it from the container in the destination operating room. FIG. 5 illustrates a fully integrated organ transport container as described herein, including organ compartment with lid above and system compartment below, secured together for transport. FIG. 6 serves to illustrate an organ transport container as described herein with an organ, in this instance represented as a human kidney, suspended in transport medium within the organ compartment.

Figure 7:
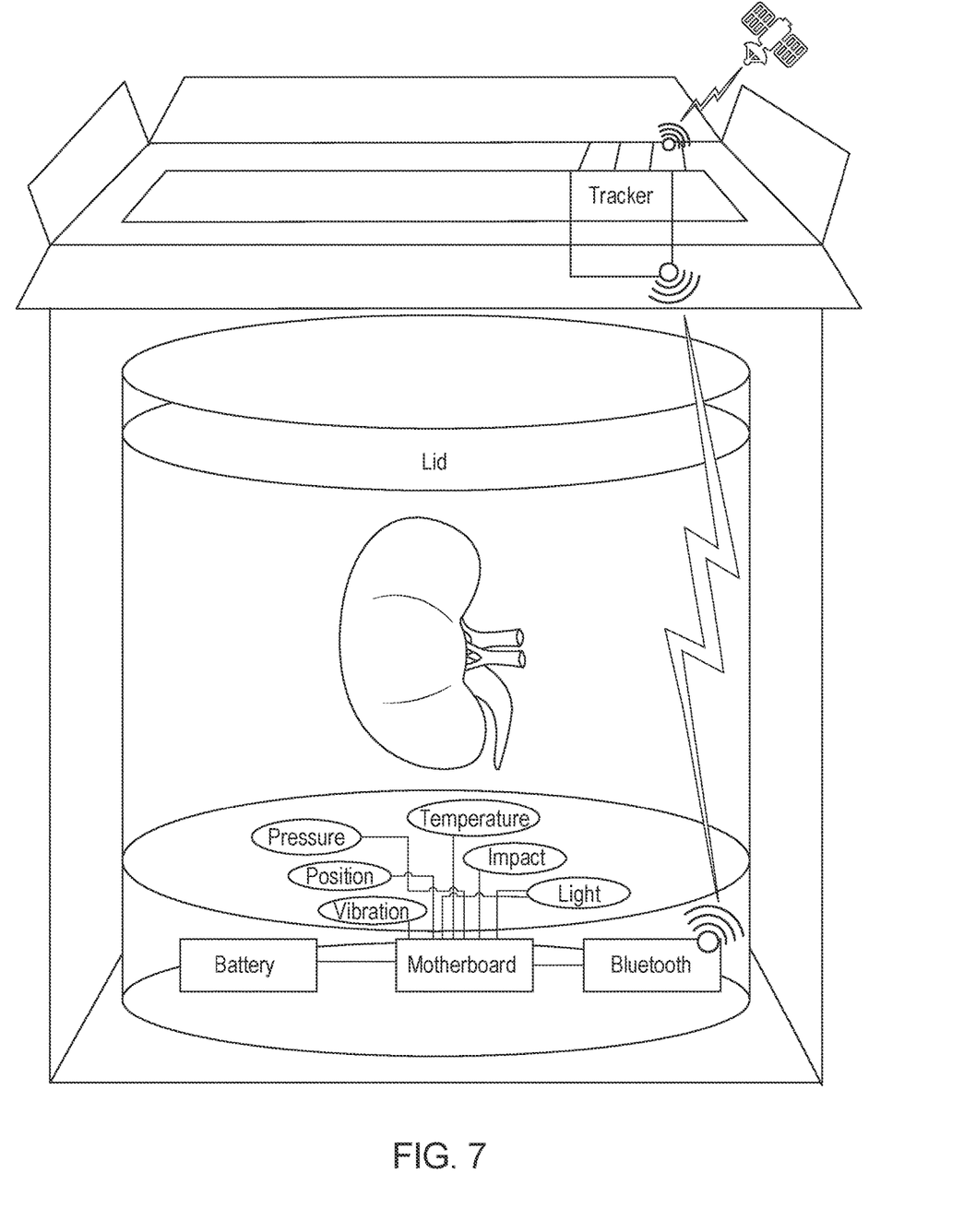
FIG. 7 illustrates the communication via transceiver between the organ transport container as shown in FIG. 6 with a location tracker, in this case external to the organ transport container but inside its external packaging.

FIG. 7 serves to illustrate an application of wireless communication technology as a feature of the invention of the present disclosure, wherein a transceiver, indicated as a Bluetooth transceiver, is able exchange data with an external tracker via short wavelength ultra-high frequency radio waves according to the Bluetooth standard. One of ordinary skill in the art will appreciate that Wi-Fi or other communication protocols may be used in an equivalent manner for data exchange with a tracker or other external device. A tracker device capable of data exchange is a preferable external data exchange component due to its satellite location tracking capability as illustrated. Thus, a tracker supplied within or about the external packaging of an organ transport container as described herein may receive and transmit data gathered from within the system compartment to a remote location via the tracker by leveraging mobile satellite technology. In this way, data from within an organ transport container according to the present invention may be transmitted in real time to its destination to enable better preparation by clinical staff in anticipation of transplant of the organ into the body of a recipient at the destination.

One of ordinary skill in the art will appreciate that communication and data storage systems external to an environmental sensing system as described herein may be placed in wireless communication a tracker according to the present disclosure and by extension the environmental sensing system itself, using modern communications protocols such as but not limited to Internet Protocol (IP), Ethernet Local Area Network (LAN) protocols, or combinations thereof. Such external systems may comprise one or more software modules tangibly stored on a non-transitory computer readable medium which when executed cause a connected microprocessor to carry out such functions as receiving data from the environmental sensing system and tracker and storing the same in a database, with or without further processing. Data stored in a database as so-described may be further processed in order to understand historical data trends associated with various environmental conditions, which may be useful in identifying correlations between various environmental conditions and the quality of the container contents when it reaches its destination, including, in the case of human organs, understanding the impact on patient outcomes in the receiving clinic.

By monitoring the environmental pressures exerted upon an asset in transit, to the extent possible and on a frequent basis, and collecting that data for multiple assets over time, a database according to certain embodiments of the present invention may be generated and analyzed for trends that allow for the rating of organs intended for transplant that may be predictive of graft success as well as the duration of recipient survival, thereby giving transplant surgeons a powerful tool to use in their decision-making processes. With the continued maturation of programmable machine learning platforms, a database can be developed that allows medical professionals to make more informed decisions with respect to how far, how long, how high, or by what means to transport an organ intended for transplant based on inputs from the donor hospital and ETAs at the transplant clinic. In one aspect, the methods described herein enable direct transmission of raw data and the findings of machine learning to statistical researchers for validation of the corollaries used to make clinical predictions, with validation techniques ultimately becoming embedded in the algorithms used to facilitate data analysis. As one of ordinary skill in the art will appreciate, skilled software developers may find new and unique ways to incorporate any manner of statistical analysis within such a rating system as enabled by the present invention in the public interest of protecting valuable national assets.

In the foregoing specification, the invention has been described with reference to exemplary systems and methods that represent discrete embodiments thereof, with a focus on improving or replacing existing transportation and logistics practices associated with human organ procurement and delivery for transplantation. As the title of the invention suggests, however, these representative embodiments contemplate broader application of the technology described herein to sensitive, high-value freight in general, and should not be assumed to be limiting to application within human organ transplantation networks. The description of various embodiments and accompanying drawings are meant to illustrate the underlying concepts but not restrict the scope of their applicability as one of ordinary skill in the art would understand within the confines of this disclosure.

The features and advantages described above will be evident to one of ordinary skill in the art. The illustrative embodiments described herein are representations of the invention and are not to be construed or interpreted as limitations to the various configurations and inclusions that may be selected for various embodiments based on the nature of transported contents, environmental conditions, transportation mode, or other factors.

What is claimed is:

1. A method for preserving the quality of a transplantable human organ in transit, the method comprising:
receiving, via a central software application in wireless communication with a tracker device associated with the organ packaged in an organ transport container, data inputs, wherein the central software application is tangibly stored on a nontransitory computer readable medium in network communication with a central processing unit (CPU), wherein the data inputs comprise an organ identifier associated with the organ, a tracker identifier associated with the tracker device for tracking a location of the organ, and a telemetric monitor identifier associated with a telemetric monitor for monitoring a local environment of the organ, and wherein the central software application comprises instructions, which when executed by the CPU, cause the CPU to:
store the data inputs in an application database;
establish network communications between the central software application and a plurality of software applications, the plurality of software applications comprising a first web service application configured to authenticate one or more user devices, a second web service application configured to receive notifications from the CPU and transmit said notifications to one or more authenticated user devices, and one or more external software applications, wherein the central software application communicates with at least the one or more external software applications over an application programming interface (API);
update the application database with real-time information communicated from the plurality of software applications, wherein the real-time information comprises one or more of geolocation, aerospace location, local weather, barometric pressure, organ position, container position, vibrational force, temperature, impact, light intensity, acceleration, or organ orientation, and wherein the real-time information is stored in relation to the data inputs;

transmit the real-time information to one or more authenticated user devices over the second web service application; and receive, from at least one of the one or more authenticated user devices, a reallocation order to reallocate the organ from a first transportation asset to a second transportation asset.

2. The method of claim 1, wherein the organ transport container comprises a system compartment housing the telemetric monitor and an organ compartment containing the organ and a transport medium for preserving the organ.

3. The method of claim 2, wherein the telemetric monitor comprises a motherboard, a transceiver, a power source, and an environmental sensor selected from the group consisting of temperature sensors, pressure sensors, position sensors, vibration sensors, acceleration sensors, impact force sensors, orientation sensors, light sensors, altitude sensors, or combinations thereof.

4. The method of claim 3, wherein the transceiver is in network communication with the tracker device.

5. The method of claim 1, wherein the organ identifier comprises one or more of an organ type, an organ donor identification, an organ donor age, an organ donor gender, an organ donor health condition, histocompatibility information, a clamp time, organ donor hospital information, organ procurement organization (OPO) information, organ sharing network (OSN) information, organ recipient hospital information, or organ recipient information.

6. The method of claim 1, wherein the at least one of the one or more authenticated user devices is associated with an authenticated user selected from the group consisting of regulatory agencies, transplant centers, OPOs, OSNs, laboratories and testing facilities, couriers, airlines, unmanned aerial system (UAS) fleet managers and combinations thereof.

7. The method of claim 1, wherein the first transportation asset is selected from the group consisting of automobiles, trains and manned aircraft, and the second transportation asset is a UAS.

8. The method of claim 1, wherein the central software application further causes the CPU to;

transmit the data inputs and the real-time information to a shipment database, the shipment database in network communication with a machine learning application tangibly stored on a nontransitory computer readable medium, wherein the machine learning application comprises instructions which, when executed by a processor, cause the processor to synthesize correlations between a quality of the organ when the organ reaches its destination and the real-time information.

9. The method of claim 8, further comprising:

statistically validating the correlations.

10. The method of claim 8, wherein the central software application causes the CPU to cause transmission of the correlations and the real-time information to one or more authenticated user devices.

11. A system for preserving the quality of a transplantable human organ in transit, the system comprising:

an organ transplant container comprising an organ compartment containing the organ and a transport medium for preserving the organ, a system compartment housing a telemetric monitor for monitoring a local environment of the organ, and a tracker device for tracking a location of the organ and for wirelessing receiving and transmitting data;

a central software application tangibly stored on a nontransitory computer readable medium in network communication with a central processing unit (CPU), the central software application configured to receive data inputs from the tracker device, the data inputs comprising an organ identifier associated with the organ, a tracker identifier associated with the tracker device, and a telemetric monitor identifier associated with the telemetric monitor, and wherein the central software application comprises instructions which, when executed by the CPU, cause the CPU to:

store the data inputs in an application database;

establish network communications between the central software application and a plurality of software applications, the plurality of software applications comprising a first web service application configured to authenticate one or more user devices, a second web service application configured to receive notifications from the CPU and transmit said notifications to one or more authenticated user devices, and one or more external software applications, wherein the central software application communicates with at least the one or more external software applications over an API;

update the application database with real-time information communicated from the plurality of software applications, wherein the real-time information comprises one or more of geolocation, aerospace location, local weather, barometric pressure, organ position, container position, vibrational force, temperature, impact, light intensity, acceleration, or organ orientation, and wherein the real-time information is stored in relation to the data inputs;

transmit the real-time information to one or more authenticated user devices over the second web service application; and receive, from at least one of the one or more authenticated user devices, a reallocation order to reallocate the organ from a first transportation asset to a second transportation asset.

12. The system of claim 11, further comprising a shipment database in network communication with the central software application and the CPU and a machine learning application tangibly stored on a nontransitory computer readable medium and comprising instructions which when executed by a processor cause the processor to synthesize correlations between the organ when the organ reaches its destination and the real-time information.

13. The system of claim 11, wherein the telemetric monitor comprises a motherboard, a transceiver, a power source, and an environmental sensor selected from the group consisting of temperature sensors, pressure sensors, position sensors, vibration sensors, acceleration sensors, impact force sensors, orientation sensors, light sensors, altitude sensors, or combinations thereof.

14. The system of claim 13, wherein the transceiver is in network communication with the tracker device.

15. The system of claim 11, wherein the first transportation asset is selected from the group consisting of automobiles, trains and manned aircraft, and the second transportation asset is a UAS.

16. The system of claim 11, wherein the organ compartment comprises one or more walls defining a first end and a second end opposite the first end, at least the first end comprising threads structured to removably secure a lid to the organ compartment.

17. The system of claim 16, wherein the second end comprises threads structured to removably secure the organ compartment to the system compartment.

18. A method for synthesizing correlations between organ quality of transplantable human organs and information generated from within a transplant distribution network, the method comprising:

receiving, via a central software application in wireless communication with a tracker device associated with an organ packaged in an organ transport container, data inputs, wherein the central software application is tangibly stored on a nontransitory computer readable medium in network communication with a central processing unit (CPU), wherein the data inputs comprise an organ identifier associated with the organ, a tracker identifier associated with the tracker device for tracking a location of the organ, and a telemetric monitor identifier associated with a telemetric monitor for monitoring a local environment of the organ, and wherein the central software application comprises instructions, which when executed by the CPU, cause the CPU to:

store the data inputs in an application database;

establish network communications between the central software application and a plurality of software applications, the plurality of software applications comprising a first web service application configured to authenticate one or more user devices, a second web service application configured to receive notifications from the CPU and transmit said notifications to one or more authenticated user devices, and one or more external software applications, wherein the central software application communicates with at least the one or more external software applications over an application programming interface (API);

update the application database with real-time information communicated from the plurality of software applications, wherein the real-time information is stored in relation to the data inputs;

transmit the data inputs and the real-time information to a shipment database, the shipment database in network communication with a machine learning application tangibly stored on a nontransitory computer readable medium, wherein the machine learning application comprises instructions which, when executed by a processor, cause the processor to synthesize correlations between a quality of the organ when the organ reaches its destination and the real-time information; and receive one or more inputs statistically validating the correlations.

19. The method of claim 18, wherein, subsequent to a transplant of the organ to a transplant recipient, the central software application further causes the CPU to:

update the shipment database with data reflecting a patient outcome associated with the transplant of the organ to the transplant recipient.

20. The method of claim 18, wherein the central software application further causes the CPU to:

update the machine learning application based on the received statistically validated correlations.

* * * * *